United States Patent [19]

King

[11] Patent Number: 5,300,282
[45] Date of Patent: Apr. 5, 1994

[54] AGENTS FOR POTENTIATING THE EFFECTS OF ANTITUMOR AGENTS AND COMBATING MULTIPLE DRUG RESISTANCE

[75] Inventor: Ann C. King, Chapel Hill, N.C.

[73] Assignee: Burroughs-Wellcome Company, Research Triangle Park, N.C.

[21] Appl. No.: 539,838

[22] Filed: Jun. 18, 1990

[30] Foreign Application Priority Data

Jun. 19, 1989 [GB] United Kingdom ............... 8914061

[51] Int. Cl.$^5$ .................. A61K 49/00; A61K 31/40; A61K 31/335; A01N 43/46
[52] U.S. Cl. .................... 424/10; 514/217; 514/265; 514/268; 514/350; 514/352; 514/427; 514/450
[58] Field of Search ............. 514/217, 265, 268, 350, 514/352, 427, 450

[56] References Cited

U.S. PATENT DOCUMENTS

| | | | |
|---|---|---|---|
| 3,420,851 | 1/1969 | Bloom et al. | 260/333 |
| 3,497,596 | 2/1970 | Ursillo | 424/244 |
| 3,993,757 | 11/1976 | Freedman | 424/244 |
| 3,996,222 | 12/1976 | Kajfez et al. | 260/247.5 D |
| 4,562,258 | 12/1985 | Findlay et al. | 546/281 |
| 4,628,047 | 12/1986 | Sakurai et al. | 514/34 |
| 4,650,807 | 3/1987 | Findlay et al. | 514/343 |
| 4,657,918 | 4/1987 | Findlay et al. | 514/318 |
| 4,690,933 | 9/1987 | Coker et al. | 514/343 |
| 4,990,538 | 2/1991 | Harris et al. | 514/648 |

FOREIGN PATENT DOCUMENTS

| | | |
|---|---|---|
| 0214779 | 3/1987 | European Pat. Off. . |
| 0187700 | 7/1987 | European Pat. Off. . |
| 0235796 | 9/1987 | European Pat. Off. . |
| 0270926 | 6/1988 | European Pat. Off. . |
| 0361485 | 4/1990 | European Pat. Off. . |
| 0363212 | 4/1990 | European Pat. Off. . |
| 0353962 | 7/1990 | European Pat. Off. . |
| 1493451 | 7/1969 | Fed. Rep. of Germany . |
| 1909408 | 11/1969 | Fed. Rep. of Germany . |
| 4016 | 3/1966 | France . |
| 61-85320 | 4/1986 | Japan . |
| 407990 | 9/1966 | Switzerland . |
| 419172 | 2/1967 | Switzerland . |
| 1018985 | 2/1966 | United Kingdom . |
| 2120941A | 12/1983 | United Kingdom . |

OTHER PUBLICATIONS

Letter from Avner Ramu, M.D., Dept. of Radiation and Clinical Oncology, Apr. 20, 1987.

*The Merck Index,* An Encyclopedia of Chemicals, Drugs, and Biologicals (11th Ed.) (Merck & Co., Inc. N.J.) 1989, p. 3192.

*Primary Examiner*—Frederick E. Waddell
*Assistant Examiner*—T. J. Criares
*Attorney, Agent, or Firm*—Bell, Seltzer, Park & Gibson

[57] ABSTRACT

Potentiating agents which enhance the efficacy of antineoplastic agents are disclosed. The potentiating agents disclosed are dibenz[b,e]oxepins such as doxepin.

4 Claims, No Drawings

AGENTS FOR POTENTIATING THE EFFECTS OF ANTITUMOR AGENTS AND COMBATING MULTIPLE DRUG RESISTANCE

FIELD OF THE INVENTION

The present invention relates to the use of dibenz[b,3]oxepin compounds as adjuvant chemotherapy for neoplasias resistant to multiple drugs. The present invention also relates to the use of such compounds as an agent for enhancing the therapeutic effect of multiple antitumor agents.

BACKGROUND OF THE INVENTION

Complete cures of various tumor like leukemias, lymphomas and solid tumors by the use of chemotherapeutic agents are rare because of heterogeneous sensitivity of tumor cells to each antitumor agent. Cancer chemotherapy also fails because of intrinsic resistance of tumors to multiple drug therapies. In other cases, a tumor may become resistant to the antitumor agents used in a previous treatment. The therapeutic effects of these agents are then eliminated. An even graver problem is that recurrent cancers are resistant not only to the cancer suppressants used in previous treatments, but also manifest resistance to other antitumor agents, unrelated to the agent used previously either by chemical structure or by mechanism of action. These phenomenon are collectively referred to as multiple drug resistance (mdr) and contribute widely to cancer treatment failures in the clinic.

The major documented cause of multiple drug resistance is overexpression of a membrane glycoprotein (the multiple drug transporter) responsible for pumping structurally diverse antitumor drugs from cells. See D. Houseman et al., *A Molecular Genetic Approach Problem of Drug Resistance in Chemotherapy*. 504–517 (1987) (Academic Press, Inc.); R. Fine and B. Chabner, *Multidrug Resistance, in Cancer Chemotherapy* 8, 117–128 (H. Pinedo and B. Chabner eds. 1986).

Tumor cells expressing elevated levels of the multiple drug transporter accumulate far less antitumor agents intracellularly than tumor cells having low levels of this enzyme. The degree of resistance of certain tumor cells has been documented to correlate with both elevated expression of the drug transporter and reduced accumulation of antitumor drugs. See M. Gottesman and I. Pastan, *J. Biol. Chem.* 263, 12163 (1988); see also A. Fojo et al., *Cancer Res.* 45, 3002 (1985). This form of multiple drug cross-resistance involves agents derived from natural products, such as the vinca alkaloids, the anthracyclines, the epipodophyllotoxins, actinomycin D and plicamycin. See I. Pastan and M. Gottesman, *New England J. Med.* 1388, 1389 Table 1 (May 28, 1987).

Adenocarcinomas derived from adrenal, kidney, liver, small intestine, and colon tissue are notorious for exhibiting inherent cross-resistance to chemically unrelated chemotherapeutic agents. See M. Gottesman and I. Pastan, supra at 12165; see also A. Fojo et al., *J. Clin. Oncol.* 5, 1922 (1987). These tissues normally express higher levels of the multidrug transporter. Other tumors documented to express high levels of the multidrug transporter include pancreatic, carcinoid, chronic myelogenous leukemia in blast crisis, and non-small cell lung carcinoma. Tumors documented to initially be drug-sensitive but to then become drug resistant include neuroblastoma, pheochromocytoma, acute lymphocytic leukemia in adults, acute nonlymphocytic leukemia in adults, nodular poorly differentiated lymphoma, breast cancer and ovarian cancers. It is estimated by the National Cancer Institute that approximately half a million tumor samples a year will be drug resistant because of aberrant levels of expression of the multidrug transporter. See L. Goldstein et al., Expression of Multidrug Resistance Gene in Human Cancers, *J. National Cancer Institute* 81, 116 (1988).

Elevated levels of expression of the mdr drug transporter in these tumors would lead to reduced intracellular levels of antitumor agents in the tumor and would cause suppression of chemotherapeutic efficacy. Tumors having elevated levels of the multiple drug transporter would require therapeutic doses of cancer suppressants far in excess of tumors exhibiting lower levels of the mdr drug transporter. Agents that inhibit the active efflux of antitumor agents by the drug transporter or agents that potentiate the efficacy of chemotherapeutic agents would enhance the activity of various antitumor agents on tumor cells. As a result of the present inventor's study, it has unexpectedly been found that when the agents disclosed herein are used together with an antitumor agent, they enhance the therapeutic effect of the antitumor agent.

A number of agents used clinically as calcium channel-blockers, calmodulin inhibitors and antiarrhythmic agents promote the activity of antitumor agents against resistant tumor cells, see Tsuruo et al., *Cancer Res.* 44, 4303 (1984); 43, 2267 (1983). Verapamil, caroverine, clomipramine, trifluoperazine, prenylamine, diltiazem, nicardipine, and quinidine enhance the activity of antitumor agents against resistant sublines of murine leukemia cells. Most agents potentiating the activity of antitumor agents are calcium antagonists, and the serious cardiotoxicities that arise during treatment have limited their clinical usefulness. While the inventor does not wish to be bound by any theory of operation for the present invention, it is noted that the agents disclosed herein are not known to have calcium antagonism. They have, however, been found to elevate the intracellular concentration of antineoplastic drugs in tumor cells overexpressing the multiple drug transporter. Sensitization of drug resistant tumors and elevation of intracellular antitumor drug concentrations probably occur by a mechanism different from calcium antagonism.

SUMMARY OF THE INVENTION

An object of the present invention is to provide an agent for enhancing the therapeutic effect of an antineoplastic agent by administering to a subject harboring a tumor a compound of FORMULA (I) below or a pharmaceutically acceptable salt thereof (hereafter referred to as the "potentiating agent")

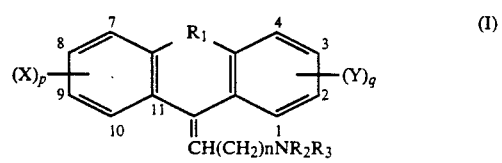

wherein:

$R_1$ is $-CH_2CH_2-$, $-CH_2O-$, $-OCH_2-$, $-NHCH_2-$, or $-CH_2NH-$;

X is hydrogen or halogen (e.g., fluorine, chlorine, bromine) attached at the 7, 8, 9 or 10 position;

Y is hydrogen or halogen (e.g., fluorine, chlorine, bromine) attached at the 1, 2, 3 or 4 position;

n is 0 to 3;

each of p and q is 1 to 4; and $R_2$ and $R_3$ independently are hydrogen, or $C_{1-4}$ alkyl, or together with the nitrogen atom form a nitrogen-containing heterocyclic ring having four to six ring members.

Preferably:

$R_1$ is —$CH_2CH_2$—, —$CH_2O$—, or —$OCH_2$—;

p and q are 1;

n is 1 or 2; and $R_2$ and $R_3$ independently are hydrogen, or $C_{1-4}$ alkyl, or taken together with the nitrogen atom form pyrrolidino.

Another aspect of the present invention is a method of increasing the sensitivity of a tumor to an antineoplastic agent when the tumor is resistant to the antineoplastic agent by administering to the subject harboring the resistant tumor a potentiating agent concurrently with an antineoplastic agent. Resistance to the antineoplastic agent may (a) be an intrinsic property of the tumor or (b) develop in response to prior treatment with the same antineoplastic agent or another antineoplastic agent capable of selecting for multi-drug resistance.

Another aspect of the present invention is a method of selectively inhibiting the growth of tumor cells in a subject in need of such treatment by concurrently administering to the subject an antineoplastic agent and a potentiating agent. The potentiating agent is administered in an amount effective to (a) reduce the amount of the antineoplastic agent required to achieve the same growth inhibiting effect on the tumor cells by the antineoplastic agent achieved without the concurrent administration of the potentiating agent; or (b) inhibit the development of multiple drug resistance in the tumor cells after treatment with the antineoplastic agent over time.

Another aspect of the present invention is a method of inhibiting multiple drug resistance in a subject in need of such treatment by administering the subject a potentiating agent in an amount effective to combat multiple drug resistance.

Another aspect of the present invention is the use of the compounds of Formula (I), or a pharmaceutically acceptable salt thereof, for the manufacture of a medicament for inhibition of multiple drug resistance in tumors.

Another aspect of the present invention is a pharmaceutical composition comprising a compound of Formula (I), or a pharmaceutically acceptable salt thereof, in combination with a pharmaceutically acceptable carrier, with the proviso that X and Y do not independently represent hydrogen, fluorine or chlorine when R is —$CH_2O$—, n is 2 and $R_2$ and $R_3$ represent hydrogen or $C_{1-4}$ alkyl.

Another aspect of the present invention is novel compounds comprising compounds of Formula (I), or the pharmaceutically acceptable salts thereof, with the provisos that: (a) when one of X and Y represent halo at the 2, 3, 8 or 9 position the other is not hydrogen; and (b) X and Y do not independently represent chlorine, fluorine or hydrogen when $R_1$ is —$CH_2O$—, n is 2 and $R_2$ and $R_3$ are hydrogen or $C_{1-4}$ alkyl.

Another aspect of the present invention is a pharmaceutical formulation comprising a potentiating agent as disclosed herein in combination with an antineoplastic agent, in a pharmaceutically acceptable carrier.

Another aspect of the present invention is the use of both the new pharmaceutical compositions disclosed above and the novel compounds disclosed above as antiasthmatic and antihistaminic agents.

DETAILED DESCRIPTION OF THE INVENTION

Potentiating agents exemplary of the present invention include:

(A) (Z)-3-(2-Bromo-6,11-dihydrodibenz [b,e]oxepin-11-ylidene)-N,N-dimethylpropylamine trihydrochloride;

(B) (E)-3-(2-Bromo-6,11-dihydrodibenz [b,e)oxepin-11-ylidene)-N,N-dimethylpropylamine 3/2 hydrochloride:

(C) (Z)-3-(9-Bromo-6,11-dihydrodibenz [b,e]oxepin-11-ylidene)-N,N-dimethylpropylamine;

(D) (Z)-3-(4-Bromo-6,11-dihydrodibenz [b,e]oxepin-11-ylidene)-N,N-dimethylpropylamine;

(E) (Z)-3-(3-Bromo-6,11-dihydrodibenz [b,e]oxepin-ylidene)-N,N-dimethylpropylamine;

(F) (Z)-1-[2-(2-Bromo-6,11-dihydrodibenz [b,e]-oxepin-11-ylidene)ethyl]pyrrolidine;

(G) (Z)-1-[3-(2-Bromo-6,11-dihydrodibenz [b,e1-oxepin-11-ylidene)propyl]pyrrolidine;

(H) (Z)-1-[2-(6,11-Dihydrodibenz[b,e]oxepin-11-ylidene)ethyl]pyrrolidine hydrochloride;

(I) (Z)-3-(2-Bromo-6,11-dihydrodibenz [b,e]oxepin-11-ylidene)-N,N-diethylpropylamine;

(J) 1-[2-(4-Bromo-6,11-dihydrodibenz [b,e]oxepin-11-ylidine)-ethyl]pyrrolidine 60% Z, 40%E;

(K) (E)-1-[3-(2-Bromo-6,11-dihydrodibenz [b,e]-oxepin-11-ylidene)propyl]pyrrolidine;

(L) (E)/(Z)-3-(8-Bromo-6,11-dihydrodibenz [b,e]-oxepine-11-ylidene)-N,N-dimethylpropylamine (80% Z:20% E);

(M) (Z)-1-[3-(9-Bromo-6,11-dihydrodibenz [b,e]-oxepin-11-ylidene)propyl]pyrrolidine;

(N) (E)-3-(2-Bromo-6,11-dihydrodibenz [b,e]oxepin-11-ylidene)-N,N-diethylpropylamine;

(O) (Z)-1-[3-(2,9-dibromo-6,11-dihydrodibenz [b,e]-oxepin-11-ylidene)propyl]pyrrolidine;

(P) (E)-3-(2-fluoro-6,11-dihydrodibenz [b.e1oxepin-11-ylidine)-N,N-dimethylpropylamine;

(Q) (Z)-3-(2-fluoro-6,11-dihydrodibenz [b,e]oxepin-11-ylidene)-N,N-dimethylpropylamine;

(R) (E)-1-[3-(2,9-dibromo-6,11-dihydrodibenz [b,e]-oxepin-11-ylidene)propyl]pyrrolidine;

(S) (E)-1-[3-(2-fluoro-6,11-dihydrodibenz [b,3]-oxepin-11-ylidene)propyl]pyrrolidine;

(T) (Z)-1-[3-(2-fluoro-6,11-dihydrodibenz [b,e]-oxepin-11-ylidene)propyl]pyrrolidine;

(U) (Z)-3-(2,9-Dibromo-6,11-dihydrodibenz [b,e]-oxepin-11-ylidene)-N,N-dimethylpropylamine;

(V) (E)-3-(2,9-Dibromo-6,11-dihydrodibenz [b,e]-oxepin-11-ylidene)-N,N-dimethylpropylamine 70% and (Z)-isomer 30%; and (W) doxepin.

The foregoing compounds are prepared in the manner described below, or are prepared by procedures which will be apparent to those skilled in the art. Compounds (A) and (B) above are disclosed in European Patent Application Publication Number 0 214 779 to L. Lever and H. Leighton, at page 6.

A compound of Formula (I) may be prepared via the Wittig method (see, e.g., U.S. Pat. Nos. 3,354,155 and 3,509,175) by reaction of a compound of Formula (II) below with a Wittig reagent.

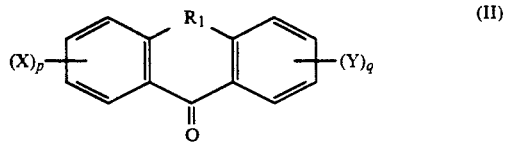

The Wittig reagent, $(C_6H_5)_3P=CH(CH_2)_nNR_2R_3$, is prepared by reacting a compound of the formula $(C_6H_5)_3PCH_2(CH_2)_nNR_2R_3Br$, with a strong base, such as sodium hydride or $C_{1-6}$ alkyl lithium, in a suitable inert solvent, such as tetrahydrofuran or dimethoxyethane, at or near room temperature.

A compound of Formula (I) also may be prepared via the Grignard reaction (see. e.g., Belg Patent No. 623,259) in which a Grignard reagent, i.e., $R^2R^3NCH_2CH_2CH_2Mg\ X$, where X is a halogen atom, is reacted with a compound of Formula (II), followed by dehydration with a strong acid.

Compounds of Formula (I) may be prepared from other compounds of Formula (I) by the exchange of halogens thereon. One method for halogen exchange is the Finkelstein halide interchange reaction. Usually, the interchange of a chlorine or bromine of aromatic rings with iodine is carried out by use of a metal iodide such as cuprous iodide, or with fluorine by use of a metal fluoride such as silver(I) fluoride in a solvent such as pyridine or quinoline or N,N-dimethylformamide with heat. A bromo compound may be converted to its corresponding chloro analogue by either use of a metal chloride such as cuprous chloride or lithium chloride in a solvent such as N,N-dimethylformamide, picoline or dimethylsulfoxide with heat (100°–103° C.), or by chlorine in radical form by radiation at temperatures of 30°–50° C. A bromo compound may also be converted to its iodo analogue by exchanging the bromine for a metal using a metal alkyl such as n-butyllithium in a ethereal solvent such as diethyl ether or tetrahydrofuran at low temperature (e.g., −78° C.), followed by reacting the metalated species with iodine cold or at room temperature or with heat to accomplish the iodination.

Compounds of Formula (I) may be prepared from compounds of Formula (III), wherein $R_1$, $R_2$, and $R_3$ are as given above, by direct halogenation.

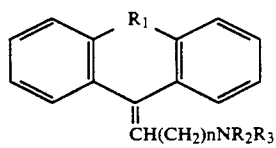

Halogenation is preferably carried out with chlorine or bromine in an inert solvent such as acetic acid, methanol, or carbon tetrachloride. In nonpolar solvents, the reaction may be catalyzed by added reagents such as hydrogen chloride and trifluoroacetic acid. The catalytic effect of trace amounts of Lewis acids added to the reaction solution may be employed, such as zinc chloride or ferric chloride in chlorinations and metallic iron, which generates $FeBr_3$ often added to Bromination mixtures. See, e.g., F. Carey and R. Sundberg, *Advanced Organic Chemistry Part B: Reactions and Synthesis*, 260-63 (1977).

A preferred category of multiple drug resistant tumor cells to be treated by the method of the present invention are multiple drug resistant cells characterized by the multidrug transporter-mediated pumping of antineoplastic agents out of the tumor cells. The multidrug transporter protein is described in M. Gottesman and I. Pastan, supra. Thus, tumor cells treated by the present invention are preferably those characterized by (a) the expression of the multidrug transporter protein at high levels, or (b) the ability to express the multidrug transporter protein upon selection by an antineoplastic agent.

Exemplary of tumor cells which express the multidrug transporter at high levels (intrinsically resistant cells) are adenocarcinoma cells, pancreatic tumor cells, carcinoid tumor cells, chronic myelogenous leukemia cells in blast crisis, and non-small cell lung carcinoma cells.

Exemplary of tumor cells having the ability to express the multidrug transporter protein upon selection by an antineoplastic agent are neuroblastoma cells, pheochromocytoma cells, adult acute lymphocytic leukemia cells, adult acute nonlymphocytic leukemia cells, nodular poorly differentiated lymphoma cells, breast cancer cells and ovarian cancer cells.

A preferred group of tumor cells for treatment in the present invention are the adenocarcinomas, including adenocarcinomas of adrenal, kidney, liver, small intestine and colon tissue, with kidney adenocarcinoma cells particularly preferred.

Preferred antineoplastic agents for use in the present invention are those to which multidrug transporter-mediated multiple drug resistant cells develop resistance. Exemplary of such antineoplastic agents are vinca alkaloids, epipodophyllotoxins, anthracycline antibiotics, actinomycin D, plicamycin, puromycin, gramicidin D, taxol, colchicine, cytochalasin B, emetine, maytansine, and amsacrine (or "mAMSA"). Preferred are vinca alkaloids, epipodophyllotoxins, anthracyclene antibiotics, actinomycin D, and plicamycin.

The vinca alkaloid class is described in *Goodman and Gilman's The Pharmacological Basis of Therapeutics*, 1277-1280 (7th ed. 1985) (hereafter "Goodman and Gilman"). Exemplary of vinca alkaloids are vincristine, vinblastine, and vindesine.

The epipodophyllotoxin class is described in Goodman and Gilman, supra at 1280-1281. Exemplary of epipodophyllotoxins are etoposide, etoposide orthoquinone, and teniposide.

The anthracycline antibiotic class is described in Goodman and Gilman, supra at 1283-1285. Exemplary of anthracycline antibiotics are daunorubicin, doxorubicin, mitoxantraone, and bisanthrene. Daunorubicin and doxorubicin are preferred.

Actinomycin D, also called Dactinomycin, is described in Goodman and Gilman, supra at 1281-1283. Plicamycin, also called mithramycin, is described in Goodman and Gilman, supra at 1287-1288.

The phrase "concurrently administering," as used herein, means that the antineoplastic agent and the potentiating agent are administered either (a) simultaneously in time (optionally by formulating the two together in a common carrier), or (b) at different times during the course of a common treatment schedule. In the latter case, the two compounds are administered at times sufficiently close for the potentiating agent to enhance the selective growth-inhibiting action of the antineoplastic agent on the tumor cells.

Subjects to be treated by the method of the present invention include both human and animal (e.g., dog, cat, cow, horse) subjects, and are preferably mammalian subjects.

The potentiating agent is administered in an amount effective to enhance the efficacy of the antineoplastic agent. The potentiating agent is preferably administered in a total amount per day of not more than about 50 mg/kg body weight, more preferably not more than about 25 mg/kg, and most preferably not more than about 5 mg/kg. With respect to minimum dose, the potentiating agent is preferably administered in a total amount per day of at least about 0.01 mg/kg, more preferably at least about 0.1 mg/kg, and most preferably at least about 1 mg/kg. The potentiating agent may be administered once or several times a day.

As noted above, the compounds of Formula (I) may be administered per se or in the form of a pharmaceutically acceptable salt. When used in medicine, the salts of the compounds of Formula (I) should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluenesulfonic, tartaric, citric, isethionic, methanesulphonic, formic, malonic, succinic, naphthalene-2-sulphonic and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical formulations, both for veterinary and for human medical use, which comprise the potentiating agent together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof.

Pharmaceutical formulations of the present invention may optionally include an antineoplastic agent, preferably an agent as described above. Such a formulation is useful for concurrently administering an antineoplastic agent and the potentiating agent in a method as described above.

The formulations include those suitable for oral, rectal, topical, nasal, ophthalmic or parenteral (including subcutaneous, intramuscular and intravenous) administration. Formulations suitable for oral and parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations of the present invention suitable for oral administration may be presented as discrete units such as capsules, cachets, tablets or lozenges, each containing a predetermined amount of the potentiating agent as a powder or granules; or a suspension in an aqueous liquor or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with a suitable carrier may be made by molding in a suitable machine.

A syrup may be made by adding the active compound to a concentrated aqueous solution of a sugar, for example sucrose to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

Formulations suitable for parenteral administration conveniently comprise a sterile aqueous preparation of the active compound, which is preferably isotonic with the blood of the recipient.

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

The new compounds and new pharmaceutical compositions of this invention have antiallergic activity and may be used for the same indications as clinically used antiasthmatic compounds, namely to help to control bronchoconstriction or bronchospasm characteristic of allergic asthma and exercise induced asthma and the symptoms of bronchoconstriction and bronchospasm resulting from acute or chronic bronchitis. The compounds and compositions are believed to inhibit the release of autocoids (i.e., histamine, serotonin and the like) from mast cells and to inhibit directly the antigen-induced production of histamine. Thus, they may be classified as mast cell stabilizers with antihistaminic action.

The new compounds and new pharmaceutical compositions of this invention have antihistamine activity, and may be used for the same indications as clinically used antihistamines, namely to relieve detrimental symptoms (caused by histamine release) of nasal stuffiness due to colds and vasomotor rhinitis and for the symptomatic control of allergic conditions including nasal allergy, perennial rhinitis, urticaria, angloneurotic oedema, allergic conjunctivitis, food allergy, drug and serum reactions, insect bites and stings and desensitizing reactions. The compounds and compositions may also be used in conditions responsive to their antipruritic activity including allergic dermatoses, neurodermatitis, anogenital pruritus, and pruritus of non-specific origin such as eczema, and of specific cause such as chickenpox, photosensitivity and sunburn. The present invention therefore provides a method for the symptomatic treatment of allergic conditions by the administration of an effective amount of the new compounds and compositions. The present invention also provides a method for the antagonism of endogenously released histamine by the administration of an effective amount of the new compounds and compositions.

The amount of active compound required for anti-asthmatic or antihistaminic use will vary with the compound chosen, the route of administration and the condition of mammal undergoing treatment, and is ultimately at the discretion of the physician. A suitable oral dose of the active compound for a mammal is in the range of from 0.003 to 1.0 milligram per kilogram body weight per day; preferably from 0.04 to 0.24 milligram per kilogram.

The desired daily dose is preferably presented as from one to six sub-doses administered at appropriate intervals throughout the day as needed. Where three sub-doses are employed, each will preferably lie in the range of from 0.014 to 0.08 milligrams per kilogram body weight; for example, a typical sub-dose of such a compound for a human recipient is between 1 and 20 milligrams, for example, 4 or 8 milligrams.

The following Examples are provided to illustrate the present invention, and should not be construed as limiting thereof. Temperatures are given in degrees Celsius unless otherwise indicated.

EXAMPLE 1

(E)/(Z)-1-[3-(2-Bromo-6,11-dihydrodibenz[b,e]oxepin-11-ylidene)propyl)pyrrolidine (Compounds K and G)

Anhydrous 3-(N-pyrrolidinyl)propyltriphenylphosphonium bromide hydrobromide (24 g, 45 mmole) was suspended in 650 ml dry tetrahydrofuran and 90 mmole of n-butyl in hexane (1.6 M) was added dropwise at 0° C. under a nitrogen atmosphere during a 30-minute period. After an additional ten minutes, 2-bromo-6,11-dihydrodibenz[b,e]oxepin-11-one (10 g, mmole), which was prepared as described in U.S. Pat. No. 4,282,365, in 100 mL dry tetrahydrofuran was added slowly to the deep red solution and the reaction mixture was then refluxed for 18 hours. The reaction mixture was poured onto ice water, and the mixture was extracted with diethyl ether. The ether layer was concentrated under reduced pressure and the residue was chromatographed on a silica gel column (Waters Associates—Prep 500) with ethyl acetate/methanol (9:1) to give the pure Z-bromopyrrolidine (1.10 g) as a yellow solid, mp 103°–104° C. pmr (DMSO-$d_6$) δ: 7.24–7.35 (m, 6H, aromatic H); 6.74 (d, J=8.4 Hz, 1H, $H_4$); 5.74 (t, 1H, CH=); 5.20 (br s, 2H, ArCH$_2$O); 2.56–2.69 (m, 8H, CH$_2$C= and 3 N—CH$_2$); 1.81 (m, 4H, 2 CH$_2$).

Analysis: Calculated for $C_{21}H_{22}BrNO$: C, 65.63; H, 5.77; N, 3.64. Found: C, 65.69; H, 5.80; N, 3.63.

This also offered the pure E-bromopyrrolidine and converted to its hydrochloride salt (0.11 g) as a white solid, mp 203°–205° C. pmr (DMSO-$d_6$) δ: 7.29–7.46 (m, 6H, aromatic H); 6.70 (d, J=8.8 Hz, 1H, $H_4$); 6.09 (t, 1H, CH=); 5.20 (br s, 2H, ArCH$_2$O); 4.31–1.02 (m, 12H, 3NCH$_2$ and 3CH$_2$).

Analysis: Calcd. for $C_{21}H_{22}BrNO.0.05 H_2O.1.3 HCl$: C, 58.30; H, 5.45; N, 3.24. Found: C, 58.21; H, 5.35; N, 3.24.

EXAMPLE 2

(E)/(Z)-1-[2-(2-Bromo-6,11-dihydrodibenz[b,e]oxepin-11-ylidene)ethyl]pyrrolidine (Compound F)

Anhydrous 2-(N-pyrrolidinyl)-ethyltriphenylphosphonium bromide (10 g, 45 mmole), 48 mmole of n-butyl lithium in hexane, and 2-bromo-6,11-dihydrodibenz [b,e]-oxepin-11-one (5 g, 35 mmole) were reacted in 300 mL dry tetrahydrofuran by the procedure in Example 1, Step a. This provided the pure Z-isomer (1.76 g) as a light brown solid, mp 108°–109° C.. pmr (DMSO-$d_6$) δ: 7.28–7.50 (m, 6H, aromatic H); 6.80 (d, J=8.8 Hz, 1H, $H_4$); 5.82 (t, 1H, HC=); 5.20 (s, 2H, ArCH$_2$O); 3.29 (m, 2H, NCH$_2$C=); 2.50 (m, 4H, 2NCH$_2$); 1.70 (m, 4H, 2CH$_2$).

Also, the pure (E)-isomer was obtained as a light-brown oil. pmr (DMSO-$d_6$) δ: 7.22–7.51 (m, 6H, aromatic H); 6.79 (d, J=8.8 Hz, 1H, H ); 6.16 (t, 1H, HC=); 5.40–5.50 (br s, 2H, ArCH$_2$O); 3.0 (m, 2H, NCH$_2$C=); 2.36 (m, 4H, 2NCH$_2$); 1.64 (m, 4H 2CH$_2$).

Analysis: Calculated for $C_{20}H_{20}BrNO$: C, 64.87; H, 5.44; N, 3.78. Found (Z-isomer): C, 64.83; H, 5.49; N, 3.75. Found (E-isomer): C, 64.79; H, 5.45; N, 3.77.

EXAMPLE 3

(E)/(Z)-3-(2-Bromo-6,11-dihydrodibenz[b,e]oxepin-11-ylidene)-N,N-diethylpropylamine (Compounds I and N)

Anhydrous 3-(diethylamino)propytriphenylphosphonium bromide hydrobromide (15 g, 28 mmole), 56 mmole of n-butyl lithium in hexane (1.6 M), and 2-bromo-6,11-dihydrodibenz [b,e]-oxepin-11-one (8.1 g, 28 mmole) were reacted in 350 mL dry tetrahydrofuran by the procedure in Example 1, Step a. This provided a (Z)/(E) (90:10) isomeric product as a brown oil. pmr (DMSO-$d_6$) δ: 7.22–7.51 (m, 6H, aromatic H); 6.78 (d, J=8.8 Hz, H4 of 90% Z); 6.68 (d, J=8.8 Hz, H of 10% of E); 6.19 (t, CH=of 10% E); 5.73 (t, CH=of 90% Z); 5.20 (br s, 2H, ArCH$_2$O); 2.30–2.60 (m, 8H, 4 CH$_2$); 0.94 (t, 6H, 2 CH$_3$ of 90% Z); 0.88 (t, 6H, 2 CH$_3$ of 10% E).

Analysis: Calculated for $C_{21}H_{24}BrNO$: C, 65.29; H, 6.26; N, 3.63; Br, 20.68. Found: C, 65.27; H, 6.26; N, 3.60; Br, 20.59.

EXAMPLE 4

(E)/(Z)-3-(2-Fluoro-6,11-dihydrodibenz[b,e]oxepin-11-ylidene)-N,N-dimethylpropylamine (Compounds Q and P)

Anhydrous 3-(dimethylamino)propyltriphenylphosphonium bromide hydrobromide (35 g, 0.07 mole), 0.14 mole of n-butyl lithium in hexane (1.6 M), and 2-fluoro-6,11-dihydrodibenz[b,e]oxepin-11-one (12 g, 0.05 mole), which was prepared as described in European patent application No. EP 38,564, were reacted in 800 mL dry tetrahydrofuran by the procedure of Example 1, Step a. This gave pure Z-isomer (0.67 g) mp 47°–48°

C. pmr(DMSO-d$_6$) δ: 6.81–7.37 (m, 7H, aromatic H), 5.73 (t, 1H, CH=), 5.14 (br s, 2H, ArCH$_2$O), 2.37–2.51 (m, 4H, 2CH$_2$), 2.09 (s, 7H, N(CH$_3$)$_2$). It also offered the pure E-isomer (1.70 g), mp 44°–45° C. pmr (DMSO-d$_6$) δ: 6.68–7.49 (m, 7H, aromatic H), 6.08 (t, 1H, CH=), 5.20 (br s, 2H, ArCH$_2$O), 2.19–2.35 (m, 4H, 2CH$_2$), 2.01 (s, 7H, N(CH$_3$)$_2$)

Analysis: Calculated for C$_{19}$H$_{20}$FNO.0.10 H$_2$O=299.17: C, 76.26; H, 6.81; N, 4.68. Found: (Z-isomer): C, 76.20; H, 6.83; N, 4.76. Found: (E-isomer): C, 76.14; H, 6.80; N, 4.69.

EXAMPLE 5

(E)/(Z)-1-[3-(2-Fluoro-6,11-dihydrodibenz[b,e]oxepin-11-ylidene)-propyl]pyrrolidine (Compounds S and T)

Anhydrous 3-(N-pyrrolidinyl)propyltriphenylphosphonium bromide hydrobromide (35 g, 0.07 mole), 0.14 mole of n-butyl lithium in hexane (1.6 M), and 2-fluoro-6,11-dihydrodibenz[b,e]oxepin-11-one (12 g, 0.05 mole), prepared as described in European Patent Application No. EP 38,564, were reacted in 800 mL dry tetrahydrofuran by the procedure described in Example 1, Step a. This offered pure Z-isomer and was converted to its hydrochloride form (3.0 g), mp 201°–202° C. pmr (DMSO-d$_6$) δ: 6.84–7.36 (m, 7H, aromatic H), 5.72 (t, 1H, CH=), 5.18 (br s, 2H, ArCH$_2$O), 3.73–1.95 (m, 12H, 3CH$_2$ and 3NCH$_2$). This also gave pure E-isomer (0.70 g), mp 77°–78° C. pmr (DMSO-d$_6$) δ: 6.69–7.50 (m, 7H, aromatic H), 6.10 (t, 1H, CH=), 5.15 (br s, 2H, ArCH$_2$O), 1.63–2.50 (m, 12H, 3CH$_2$ and 3NCH$_2$).

Analysis: Calculated for C$_{21}$H$_{22}$FNO.0.96 HCl.0.04 H$_2$O: C, 70.23, H, 6.47; N, 3.90; Cl, 9.48. Found: (Z-isomer): C, 69.96; H, 6.68; N, 3.77; Cl, 9.36. Calculated for C$_{21}$H$_{22}$FNO.0.50 H$_2$O: C, 75.88; H, 6.97; N, 4.21. Found: (E-isomer): C, 76.03; H, 6.79; N, 4.43.

EXAMPLE 6

(E)/(Z)-3-(3-Bromo-6,11-dihydrodibenz[b,e]oxepin-11-ylidene)-N,N-dimethylpropylamine (Compound E)

(a) Methyl 2-(3-bromophenoxymethyl)benzoate

To a mixture of 3-bromophenol (60 g, 0.35 mole) and potassium carbonate (25 g, 0.18 mole) in 250 mL of N,N-dimethylformamide was added methyl α-bromo-2-toluate (65 g, 0.28 mol). The reaction mixture was stirred at room temperature for 18 hours, then heated on a stream bath for three hours. The mixture was poured into ice water, and the solids were collected by filtration and washed with water to give the crude product. Analytical sample was obtained by recrystallization from methylene chloride/hexanes, m.p. 84°–85° C. prm (CDCl$_3$) δ: 8.0 (m, 1H, H$_6$), 6.93–7.69 (m, 7H, aromatic H), 5.47 (s, 2H, ArCH$_2$O), 3.89 (s, 3H, CO$_2$CH$_3$)

Analysis: Calculated for C$_{15}$H$_{13}$BrO$_3$: C, 56.09; H, 4.08; Br, 24.88. Found: C, 56.20; H, 4.12; Br, 24.77 b) 2(3-bromophenoxymethyl)benzoic acid

Methyl 2-(3-bromophenoxymethyl)benzoate (34 g) was refluxed in a mixture of 100 mL of 10% sodium hydroxide and 200 mL of methanol for three hours. The reaction mixture was concentrated under reduced pressure and water was added to the residue. The mixture was then acidified with concentrated hydrochloric acid. Extracting the acidic solution with ethyl acetate and then concentration of the organic layer gave 2-(3-bromophenoxymethyl) benzoic acid (35 g) m.p. 158°–159° C. pmr (CDCL$_3$) δ: 8.10 ()m, 1H, H$_6$), 6.84–7.74 (m, 7H, aromatic H), 6.16 (br s, 1H, CO$_2$H), 5.49 (s, 2H, ArCH$_2$O).

Analysis: Calculated for C$_{14}$H$_{11}$rO$_3$: C, 54.74; H, 3.61; Br, 26.02. Found: C, 54.65; H, 3.61; Br, 26.08.

c) 3-bromo-6,11-dihydrodibenz[b,e]oxepin-11-one

A suspension of 2-(3-bromophenoxymethyl)benzoic acid (35 g, 0.11 mole) in 100 mL of trifluoracetic anhydride containing 20 drops of boron trifluoride-ether complex was refluxed for four hours. The mixture was poured into ice water and then extracted with diethyl ether. Concentration of ether solution under reduced pressure and chromatography of the residue on a silica gel column (Waters Associates, Prep 500) with hexane/methylene chloride (70:30) gave the pure product (14 g), m.p. 110°–112 C. pmr (CDCL$_3$) δ: 8.10 (d, J=9.1 Hz, 1H, H$_1$), 7.90 (dd, J=1.4, 7.6 H, 1H, H$_{10}$) 7.57 (dt, J=1.4, 7.4, 7.4 Hz, 1H, H$_8$), 7.48 (dt, J=1.4, 7.6, 7.6 Hz, 1H, H$_9$), 7.36 (dd, J=1.3, 7.3 Hz, 1H, H$_7$), 7.27 (d, J=1.8 H, 1H, H$_4$), 7.24 (dd, J=1.8, 9.1 Hz, 1H, H$_2$), 5.18 (s, 2H, ArCH$_2$O).

Analysis: Calculated for C$_{14}$H$_9$BrO$_2$: C, 58.16; H, 3.14; Br, 27.64. Found: C, 58.13; H, 3.19; Br, 27.72.

d) (E)//Z)-3-(3-Bromo-6,11-dihydrodibenz[b,e]-oxepin-11-ylidene)-N,N-dimethylpropylamine Anhydrous 3-(dimethylamino)propyltriphenylphosphonium bromide hydrobromide (24.5 g, 48.0 mmole), 96 mmole of n-butyl lithium in hexane, and 3-bromo-6,11-dihydrodibenz[b,e]oxepin-11-one (10 g, 34.6 mmole) were reacted in 580 mL dry tetrahydrofuran by the procedure of Example 1, Step a. This provided a Z/E(3:1) isomeric mixture of bromoamines (6.0 g). Recrystallization of half of the mixtures (3.0 g) from ethyl acetate gave 1.45 g of Z-isomer of ≧93% stereoisomeric purity (assayed by 'H-NMR) and converted to its hydrochloride salt as a white solid. pmr (CDCl$_3$) δ: 7.23–7.31 (m, 4H, aromatic H), 6.92–7.05 (m, 3H, aromatic H), 5.91 (t, 1H, CH=, 7% E-isomer), 5.60 (t, 1H, CH=, 93% Z-isomer), 5.15 (Very br s, 2H, ArCH$_2$O), 3.12 (m, 2H, CH$_2$), 2.99 (m, 2H, NCH$_2$), 2.78 (s, 6H, NMe$_2$, 93% Z-isomer), 2.71 (s, 6H, NMe$_2$ 3% E-isomer).

Analysis: Calculated for C$_{19}$H$_{20}$BrNO.1.0 HCl: C, 57.81; H, 5.36; N, 3.55. Found: C, 57.62; H, 5.33; N, 3.54.

EXAMPLE 7

(E)/(Z)-3-(4-Bromo-6,11-dihydrodibenz[b,e]oxepin-11-ylidene)-N,N-dimethylpropylamine (Compound D)

(a) Methyl 2-(2-bromophenoxymethyl)benzoate

Methyl α-bromo-2-toluate (53 g, 0.23 mole) was added to a mixture of 2-bromophenol (40 g, 0.23 mole) and potassium carbonate (42 g, 0.3 mole) in 250 mL of N,N-dimethylformamide. The reaction mixture was stirred at room temperature for 18 hours, then heated on a steam bath for 3.5 hours. The mixture was poured into ice water, and the solids were collected by filtration and washed with water to give the crude product. An analytical sample was obtained by recrystallization from hexane/ethyl acetate (38 g, mp 73°–74° C. pmr (CDCl$_3$) δ: 6.58–8.05 (m, 8, aromatic H); 5.48 (s, 2H, ArCH$_2$O); 3.80 (s, 3H, CO$_2$CH$_3$)

Analysis: Calculated for C$_{15}$H$_{13}$BrO$_3$: C, 56.09; H, 4.08; Br, 24.88. Found: C, 56.12; H, 4.09; Br, 24.85.

(b) 2-(2-bromophenoxymethyl)benzoic acid

Methyl 2-(2-bromophenoxymethyl) benzoate (38 g) was refluxed in a mixture of 100 mL of 10% aqueous sodium hydroxide and 200 mL of methanol for three hours. The reaction mixture was concentrated under reduced pressure and water was added to the residue. The mixture was then acidified with concentrated hydrochloric acid. Extraction of the cooled acidic solution with ethyl acetate and then concentration of the organic layer gave 2-(2-bromophenoxymethyl)benzoic acid (30 g), mp 175°–177° C. pmr (CDCl$_3$) δ: 6.79–8.02 (m, 8H, aromatic H); 5.53 (s, 2H, ArCH$_2$O).

Analysis: Calculated for $C_{14}H_{11}BrO_3$: C, 54.74; H, 3.61; Br, 26.02. Found 54.64; H, 3.61; Br, 26.14.

(c) 4-Bromo-6,11-dihydrodibenz[b,e]oxepin-11-one

A suspension of 2-(2-bromophenoxymethyl)benzoic acid (18.8 g, 0.06 mole) in 100 mL of trifluoracetic anhydride containing ten drops of boron trifluoride-ether complex was refluxed for four hours. The mixture was poured into ice water and then extracted with diethyl ether. Concentration of the ether solution under reduced pressure gave the pure product (9.2 g), mp 127°–130° C. pmr (CDCl$_3$) δ: 7.28–8.19 (m, 76H, aromatic H); 6.99 (t, 1H, H$_2$); 5.30 (s, 2H, ArCH$_2$O).

Analysis: Calculated for $C_{14}H_9BrO_2$: C, 56.16; H, 3.14; Br, 27.64. Found: C, 58.19; H, 3.18; Br, 27.68.

(d) (E)/(Z)-3-(4-Bromo-6,11-dihydrodibenz[b,e]-oxepin-11-ylidene)-N,N-dimethylpropylamine hydrochloride Anhydrous 3-(dimethylamino)propyltriphenylphosphonium bromide hydrobromide (22.5 g, 0.04 mole) was suspended in 550 mL of dry tetrahydrofuran, and 55 mL of a solution of n-butyl lithium in hexane (1.6 M) was added dropwise at 0° C. under a nitrogen atmosphere during a 30-minute period. After an additional ten minutes, 4-bromo-6,11-dihydrodibenz[b,e]oxepin-11-one (9.2 g, 0.03 mole) in 100 mL of dry tetrahydrofuran was added slowly to the deep red solution and the reaction mixture was then refluxed for 18 hours. The reaction mixture was poured into ice water, and the mixture was extracted with ethyl ether. The ether layer was concentrated under reduced pressure and the residue was suspended in water and then acidified with 6 N hydrochloric acid. The acidic aqueous layer was washed with hexane and then was concentrated to give a gummy residue. It was chromatographed on a silica gel column (Waters Associates - Prep 500) with ethyl acetate/methanol (8:2) to give 5.2 g of product as a mixture of Z/E-isomers (approximately 95:5), mp >200° C. (grad. dec.). pmr (CDCl$_3$) δ: 7.56 (dd, 1H, H$_3$); 7.30–7.42 (m, 4H, aromatic H); 7.20 (dd, 1H, H$_1$); 6.92 (t, 1H, H$_2$); 5.72 (t, 1H, CH=); 5.32 (br s, 2H, CH$_2$O); 3.20 (t, 2H, CH$_2$N); 2.68 (m, 2H, CH$_2$); 2.70 (s, 6H, N(CH$_3$)$_2$); 5% of (E)-isomer by δ6.08 (t, 1H, CH=) and 2.64 (s, 6H, N(CH$_3$)$_2$).

Analysis: Calculated for $C_{19}H_{20}BrNO \cdot HCl \cdot 0.4\ H_2O$: C, 56.78; H, 5.47; N, 3.48. Found: C, 56.93; H, 5.30; N, 3.51.

EXAMPLE 8

(E)/(Z)-1-[2-(4-Bromo-6,11-dihydrodibenz[b,e]oxepin-11-ylidene)-ethyl]pyrrolidine (Compound J)

Anhydrous 2-(N-pyrrolidinyl)ethyltriphenylphosphonium bromide (20 g, 45 mmole), 45 mmole of n-butyl lithium in hexane (1.6 M), and 4-bromo-6,11-dihydrodibenz[b,e]oxepin-11-one (10 g, 35 mmole) were reacted in 550 mL dry tetrahydrofuran by the procedure in Example 1, Step a. This offered a (Z)/(E) (60:40) isomeric product as a light brown oil. pmr (DMSO-d$_6$)δ: 7.28–7.56 (m, 5H, aromatic H); 7.15–7.26 (2 dd, 1H, H$_1$); 6.88 (t, H$_3$ of 60% Z); 6.84 (t, H$_3$ of 40% E); 6.16 (t, CH= of 40% E); 5.86 (t, CH= of 60% Z); 5.30 (br s, 2H, ArCH$_2$O); 2.28–2.54 (m, 6H, N(CH$_2$)$_3$); 1.66 (m, 4H, 2CH$_2$).

Analysis: Calculated for $C_{20}H_{20}BrNO$: C, 64.87; H, 5.44; N, 3.78; Br, 21.58. Found: C, 64.84; H, 5.46; N, 3.77; Br, 21.68.

EXAMPLE 9

(E)/(Z)-3-(8-Bromo-6,11-dihydrodiebenz[b,e]oxepin-11-ylidene)-N,N-dimethylpropylamine (Compound L)

(a) 8-Bromo-6,11-dihydrodibenz[b,e]oxepin-11-one

Phenol (8 g, 85 mmole) and potassium carbonate (11.7 g, 85 mmole) in 150 mL of N,N-dimethylformamide was reacted with methyl 4-bromo-α-bromo- 2-toluate (20 g, 65 mmole) by the procedure of Example 6, step a and followed with alkaline hydrolysis by the procedure of Example 6, step b to give the crude 4-bromo-2-(phenoxymethyl)benzoic acid (13 g) which was used without further purification.

The crude 4-bromo-2-(phenoxymethyl)benzoic acid (13 g, 42 mmole) was cyclized in 50 mL of trifluroacetic anhydride containing 1 mL of boron trifluorideether complex by the procedure of Example 6, step c. The solid was collected by filtration and washed with water to give 11.9 g of the tricyclic ketone, m.p. 125°–126° C. pmr (CDCL$_3$) δ: 8.17–8.30 (m, 1H, H$_1$), 6.99–7.86 (m, 6H, aromatic H), 5.14 (s, 2H, ArCH$_2$O).

Analysis: Calculated for $C_{14}H_9BrO_2$: C, 58.16; H, 3.14; Br, 27.64. Found: C, 58.15; H, 3.17; Br, 27.73.

(b) (E)/(Z)-3-/8-Bromo-6,11-dihydrodibenz[b,e]-oxepin-11-ylidene)-N,N-dimethylpropylamine Anhydrous 3-(dimethylamino)propyltriphenylphosphonium bromide hydrobromide (24.5 g, 48 mmole), 96 mmole of n-butyl lithium in hexane (1.6 M), and 8-bromo-6,11-dihydrodibenz[b,e]oxepin-11-one (10 g, 34.6 mmole) were reacted in 580 mL dry tetrahydrofuran by the procedure of Example 1, Step a. This provided an E/Z (1:3.5) isomeric mixture of bromoamines. Recrystallization of the mixture from diethyl ether gave 0.17 g of Z-isomer and 1.8 g of an E/Z (1:4) (assayed by HPLC on C18) isomeric mixture. pmr (Z-isomer) (CDCl$_3$) δ: 7.38–7.44 (m, 2H, H$_7$ and H$_9$); 7.13–7.18 (m, 3H, aromatic H); 6.84–6.93 (m, 2H, H$_2$ and H$_4$); 5.70 (t, 1H, CH=); 5.15 (br s, 2H, ArCH$_2$O); 2.55 (q, 2H, CH$_2$); 2.43 (t, 2H, NCH$_2$); 2.22 (s, 6H, NMe$_2$).

Analysis: Calculated for $C_{19}H_{20}BrNO$: C, 63.70; H, 5.63; N, 3.91. Found (Z-isomer): C, 63.85; H, 5.65; N, 3.92.

EXAMPLE 10

(E)/(Z)-3-(9-Bromo-6,11-dihydrodibenz[b,e]oxepin-11-ylidene)-N,N-dimethylpropylamine (Compound C)

Anhydrous 3-(dimethylamino)propyltriphenylphosphonium bromide hydrobromide (35 g, 69 mmole), 100 mmole of n-butyl lithium in hexane (1.6 M), lo and 9-bromo-6, 11-dihydrodibenz[b,e]oxepin-11-one (20 g, 69 mmole) were reacted in 750 mL dry tetrahydrofuran by the procedure of Example 1, Step a. Recrystallization of the mixture from chloroform/carbon tetrachloride gave 6.7 g of the product (Z:E=93.7) as its hydrochloride salt, melting range 85°–88° C. pmr (CDCl$_3$) δ: 6.94–7.46 (m, 7H, aromatic), 6.04 (t, CH= of 7% E), 5.64 (t, CH= of 93% Z), 5.15 (br s, 2H, CH$_2$O), 3.07 (m, 4H, NCH$_2$ CH$_2$), 2.75 (s, 6H, NMe$_2$).

Analysis: Calculated for C$_{19}$H$_{20}$BrNO.2.0 HCl.0.3 H$_2$O: C, 52.27; H, 5.22; N, 3.21. Found: C, 52.28; H, 5.23; N, 3.18.

EXAMPLE 11

(E)/(Z)-1-[3-(9-Bromo-6,11-dihydrodibenz[b,e]oxepin-11-ylidene)propyl]pyrrolidine (Compound M)

Anhydrous 3-(N-pyrrolidinyl)propyltriphenylphosphonium bromide hydrobromide (40 g, 0.08 mole), 0.16 mole of n-butyl lithium in hexane (1.6 M), and 9-bromo-6,11-dihydrodibenz[b,e]oxepin-11-one (20 g, 0.07 mole) were reacted in 900 mL dry tetrahydrofuran by the procedure described in Example 1, Step a. This provided 8.15 g of Z/E (5:1) mixture of 9-bromopyrrolidine which was converted to its hydrochloride salt. The isomeric mixture was washed with hot ethyl acetate to give 6.0 g of the product (Z:E=93:7) as a white solid, m.p. 214°–2–17° C. pmr (DMSO-d$_6$) δ: 6.94–7.56 (m, 6 H, aromatic H), 6.86 (dd, H of 93% Z), 6.14 (dd, H$_4$ of 7% E), 6.08 (t, CH= of 7% E), 6.08 (t, CH= of 7% E), 5.76 (t, CH= of 93% Z), 5.20 (br s, 2H, ArCH$_2$O), 1.90–3.32 (m, 12H, 6CH$_2$).

Analysis: Calculated for C$_{21}$H$_{22}$BrNO.1.6 HCl: C, 56.98: H, 5.37; N, 3.16. Found: C, 56.89,; H, 5.32; N, 3.05.

EXAMPLE 12

(E)/(Z)-3-(2,9-Dibromo-6,11-dihydrodibenz[b,e]oxepin-11-ylidene)-N,N-dimethylpropylamine (Compounds V and U)

(a) Methyl 5-bromo-2-(4-bromophenoxymethyl)benzoate

To a mixture of 4-bromophenol (50 g, 0.29 mole) and sodium hydride (14 g, 0.36 mole) in 500 mL of N,N-dimethylformamide was added o-5-dibromo-2-toluate (74 g, 0.24 mole). The reaction mixture was stirred at 40° C. for 18 hours. The mixture was poured into ice water and the solids were collected by filtration and washed with water to give the product (90 g). Analytical sample was obtained by recrystallization from ethyl acetate, mp 101°–102° C. pmr (DMSO-d$_6$) δ: 6.90–8.01 (m, 7H, aromatic H), 5.35 (s, 2H, ArCH$_2$O), 3.81 (s, 3H, CO$_2$CH$_3$)

Analysis: Calculated for C$_{15}$H$_{12}$Br$_2$O$_3$.0.20 EtoAc: C, 45.43; H, 3.28; Br, 38.26. Found: C, 45.42; H, 3.10; Br, 38.61.

(b) 5-Bromo-2-(4-bromophenoxymethyl)benzoic acid

Methyl 5-bromo-2-(4-bromophenoxymethyl)benzoate (90 g, 0.23 mole) was refluxed in a mixture of 100 mL of 10% sodium hydroxide and 200 mL of methanol for three hours. The reaction mixture was concentrated under reduced pressure and water was added to the residue. The mixture was acidified with concentrated hydrochloric acid. A solid was precipitated and collected as the acid product (80 g). mp 214°–215° C. pmr (DMSO-d$_6$) δ: 6.76–8.01 (m, 7H, aromatic H), 5.38 (s, 2H, ArCH$_2$O).

(c) 2,9-Dibromo-6,11-dihydrodibenz[b,e]oxepin-11-one

A solution of 5-bromo-2-(4-bromophenoxymethyl)-benzoic acid (100 g, 0.26 mole), and trifluoroacetic anhydride (160 mL) in one liter of methylene chloride containing 20 drops of boron trifluoride-ether complex was refluxed for three hours. The mixture was poured into ice water and then extracted with diethyl ether. Concentration of ether solution under reduced pressure and chromatography of the residue on a silica gel column (Waters Associates, Prep 500) with hexane/ethyl acetate (9:1) gave the ketone (45 g) mp 193°–194° C. pmr (DMSO-d$_6$) δ: 8.12 (d, J=2.7 Hz, 1H, H$_{10}$), 7.27–7.91 (m, 4H, aromatic H), 7.10 (d, J=8.8 Hz, 1H, H$_4$), 5.32 (s, 2H, ArCH$_2$O).

Analysis: Calculated for C$_{14}$H$_8$Br$_2$O$_2$: C, 45.69; H, 2.19; Br, 43.42. Found: 45.49; H, 2.22; Br, 43.27.

(d) (E)/(Z)-3-(2,9-Dibromo-6,11-dihydrodibenz[b,e]-oxepin-11-ylidine)-N,N-dimethylpropylamine Anhydrous 3-(dimethylamino)propyltriphenylphosphonium bromide hydrobromide (27 g, 0.05 mole), 0.1 mole of n-butyl lithium in hexane (1.6 M), and 2,9-dibromo-6,11-dihydrodibenz[b,e]oxepin-11-one (15 g, 0.04 mole) were reacted in 650 mL dry tetrahydrofuran by the procedure of Example 1, Step a. This provided an (E)/(Z) isomeric mixture of dibromoamine. Separation of this mixture by a silica gel column (Waters Associates - Prep 50) with ethyl acetate/methanol (9:1) offered the Z-isomer (5.4 g). mp 87°–88° C., pmr (DMSO) δ: 7.31–7.54 (m, 5H, aromatic H), 6.78 (d, J=8.9 Hz, 1H, H$_4$), 5.77 (t, 1H, CH=), 5.15 (br s, 2H, ArCH$_2$O), 2.40 (m, 4H, 2 CH$_2$), 2.10 (s, 6H, N(CH$_3$)$_2$) And a Z/E mixture (30:70) which was converted to its hydrochloride salt by adding one equivalent hydrochloric acid (0.18 g), mp 113°–115° C. pmr (DMSO-d$_6$) δ: 7.28–7.78 (m, 5H, aromatic H), 6.82 (d, J=8.8 Hz, H of 30% E), 6.71 (d, J=8.8 Hz, H$_4$ of 70% E), 6.04 (t, CH= of 70% E), 5.76 (t, CH= of 30% Z), 4.90–5.50 (m, 2H, ArCH$_2$O), 2.30–3.19 (m, 10H, 2 CH$_2$ and N(CH$_3$)$_2$).

Analysis: Calculated for C$_{19}$H$_{19}$Br$_2$NO: C, 52.20; H, 4.28; N, 3.20; Br, 36.55.

Found (Z-isomer): C, 52.40; H, 4.40; N, 3 29; Br, 36.39. Calculated for C$_{19}$H$_{19}$Br$_2$NO.HCl: C, 48.18; H, 4.26; N, 2.96. Found (Z/E=30:70): C, 48.57; H, 4.66; N, 2.68.

EXAMPLE 13

(E)/(Z)-1-[3-(2,9-Dibromo-6,11-dihydrodibenz[b,e]oxepin-11-ylidene)propyl]pyrrolidine (Compounds R and O)

Anhydrous 3-(N-pyrrolidinyl)propyltriphenylphosphonium bromide hydrobromide (47 g, 0.08 mole), 0.20 mole of n-butyl lithium in hexane (1.6 M), and 2,9-dibromo-6,11-dihydrodibenz[b,e]oxepin-11-one (25 g, 0.07 mole) in one liter of dry tetrahydrofuran by the procedure of Example 1, Step a. The crude product was chromatographed on a silica gel column (Waters Associates - Prep 500) with ethyl acetate/methanol (95:5) to give the product as 98% pure Z-isomer (0.30 g), mp 102°–103° C. pmr (DMSO-d$_6$) δ: 7.31–7.54 (m, 5H, aromatic H), 6.79 (d, J=7.8 Hz, H$_4$ of 98% Z), 6.67 (d, J=7.8 Hz, H of 2% E), 6.11 (t, CH= of 2% E), 5.78 (t, CH= of 98% Z), 2.34–2.56 (m, 8H, CH$_2$ and 3NHCH$_2$), 1.63 (m, 4H, 2CH$_2$). And it gave another batch of the product as 90% pure E-isomer (0.18 g), mp 115°–116° C., pmr (DMSO) δ: 7.71–7.68 (m, 5H, aromatic H), 6.80 (d, J=7.8 Hz, H$_4$ of 10% Z), 6.70 (d, J=7.8 Hz, H$_4$ of 90% E), 6.10 (t, CH= of 90% E), 5.81 (t, CH= of 10% Z), 2.26–2.40 (m, 8H, CH$_2$ and 3NCH$_2$), 1.60 (m, 4H, 2CH$_2$).

Analysis: Calculated for $C_{21}H_{21}Br_2NO$: C, 54.45; H, 34.57; N, 3.02, Br, 34.50. Found (Z/E=98:2): C, 54.51; H, 4.59; N, 3.01; Br, 34.45. Found (Z/E=10:90): C, 54.51; H, 4.57; N, 3.04; Br, 34.40.

EXAMPLE 14

(Z)-1-[2-(6,11-Dihydrodibenz[b,e]oxepin-11-ylidene)ethyl]pyrrolidine (Compound H)

A solution of n-butyl lithium in hexane (1.6 M, 3 mL) was added dropwise to a solution of 1.5 g pure (Z)-1-[2-(2-bromo-6,11-dihydrodibenz[b,e]-oxepin-11-ylidene)ethyl]pyrrolidine in 100 mL of dry tetrahydrofuran at −70° C. under a nitrogen atmosphere. After the yellowish orange solution was stirred at −70° C. for ten minutes, gaseous carbon dioxide was bubbled through the reaction medium to give a pale yellow solution. The solution was allowed to warm gradually to room temperature and was then concentrated under reduced pressure. None of the carbonylated products were able to be detected by HPLC on C18. The foamy residue was suspended in water, and the solids were collected by filtration. The solid obtained was recrystallized from water to give debrominated Z-isomer (0.08 g), m.p. 203°–205° C. pmr ($CD_3OD$) δ: 7.30–7.40 (m, 4H, aromatic H); 7.24–7.27 (m, 1H, aromatic H); 6.90–7.07 (m, 3H, aromatic H); 5.84 (t, 1H, CH=); 5.25 (br s, 2H, $ArCH_2O$); 4.19 (d, J=6.5 Hz, 2H, $NCH_2C$=); 3.30 (m, 4H, $2NCH_2$); 2.04 (m, 4H, $2CH_2$).

Analysis: Calculated for $C_{20}H_{21}NO\cdot 1.25\ H_2O$: C, 68.56; H, 7.05; N, 4.00. Found: C, 68.62; H, 6.94; N, 3.98.

EXAMPLE 15

In Vitro Cytotoxicity of Potentiating Agents in Chinese Hamster Ovary Cells

Chinese hamster ovary (CHO) tissue culture cells were obtained from Dr. Vic Ling, Princess Margaret Hospital, Toronto, Canada. The parental cell line (AuxBl) and a multidrug resistant line (C5S32) having an amplified form of the MDR drug transport protein were plated into 96-well microtitre culture dishes at 250 or 500 cells per well in minimal essential medium, type alpha, 10% fetal calf serum and incubated in 95% oxygen/5% carbon dioxide for 48 hours. After this period, the medium was changed and one-half of the culture was treated with Actinomycin D (Act D) (0.01 μM for AuxBI cells and 0.5 μM or C5S32 cells). C5S32 cells are about 200-fold resistant to Actinomycin D compared to the parental AuxBl cell line. In addition to Act D some of the cultures also received a dose of the potentiating agent at 1 and 10 μM. Thus, four conditions were tested in each screening assay: untreated cells in medium alone, cells receiving Act D alone, cells incubated with the potentiating agent alone, and cells incubated with a combination of Act D and the potentiating agent. Both the parental and mdr cell lines were treated with these four conditions simultaneously. Each experimental condition reported below is based on the average absorbance from eight replicate samples. The incubation with Act D and the test drug continued for 96 additional hours, after which 0.5 mg/ml MTT dye was added to the cultures and allowed to incubate for three hours. The cells were solubilized by addition of DMSO and the absorbance at 570 nm was monitored. The absorbance is directly related to the number of surviving cells in the culture dish.

In Table 1 below, the absorbance was normalized so that cytotoxicity of the potentiating agent could be evaluated. Untreated cultures were given a value of 1.00 and the cultures receiving 1 and 10 μM of the potentiating agent are reported as a fraction of this value. To evaluate the compounds for inducing synergism with Actinomycin D, the absorbance values of cultures receiving Act D alone were assigned a value of 1.00 and cultures receiving the combination of Act D and potentiating agent Act D are reported as a fraction of this control. In most experiments, this concentration of Act D gave a reduction in cell number 10–20% below the value of completely untreated cultures.

TABLE 1

In Vitro Cytotoxicity of Potentiating Agents in Chinese Hamster Ovary Cells

| Compound | Dose | Wildtype AUXB1 | | Drug Resistant C5S32 | |
|---|---|---|---|---|---|
| | | 0 | +ACT D | 0 | +ACT D |
| (A) | 1 μM | 1.00 | 1.00 | 0.85 | 0.71 |
| | 10 μM | 1.00 | 0.99 | 0.42 | 0.22 |
| (B) | 1 μM | 0.98 | 1.00 | 0.83 | 0.82 |
| | 10 μM | 0.87 | 0.62 | 0.55 | 0.37 |
| (C) | 1 μM | 1.00 | 0.92 | 1.00 | 0.90 |
| | 10 μM | 0.92 | 0.95 | 1.00 | 0.54 |
| (D) | 1 μM | 1.00 | 1.00 | 0.89 | 0.71 |
| | 10 μM | 1.00 | 0.99 | 0.34 | 0.31 |
| (E) | 1 μM | 1.00 | 1.00 | 0.85 | 0.66 |
| | 10 μM | 1.00 | 0.98 | 0.48 | 0.35 |
| (F) | 1 μM | 1.00 | 0.96 | 0.82 | 0.68 |
| | 10 μM | 0.88 | 0.64 | 0.28 | 0.19 |
| (G) | 1 μM | 1.00 | 1.00 | 0.54 | 0.47 |
| | 10 μM | 1.00 | 0.65 | 0.15 | 0.10 |
| (H) | 1 μM | 1.00 | 1.00 | 0.82 | 0.95 |
| | 10 μM | 0.94 | 0.92 | 0.53 | 0.51 |
| (I) | 1 μM | 0.90 | 0.89 | 0.95 | 0.77 |
| | 10 μM | 0.92 | 0.21 | 1.00 | 0.36 |
| (J) | 1 μM | 1.00 | 0.90 | 0.80 | 0.66 |
| | 10 μM | 1.00 | 0.83 | 0.29 | 0.12 |
| (K) | 1 μM | 0.83 | 0.82 | 1.00 | 0.79 |
| | 10 μM | 0.87 | 0.03 | 1.00 | 0.28 |
| (L) | 1 μM | 0.83 | 0.88 | 0.92 | 0.85 |
| | 10 μM | 0.81 | 0.60 | 0.99 | 0.42 |
| (M) | 1 μM | 0.79 | 0.88 | 0.86 | 0.83 |
| | 10 μM | 0.84 | 0.47 | 1.00 | 0.35 |
| (N) | 1 μM | 0.86 | 0.85 | 1.00 | 0.85 |
| | 10 μM | 0.83 | 0.46 | 0.80 | 0.33 |
| (O) | 1 μM | 1.00 | 1.00 | 0.48 | 0.58 |
| | 10 μM | 0.93 | 0.90 | 0.35 | 0.38 |
| (P) | 1 μM | 1.00 | 1.00 | 0.61 | 0.70 |
| | 10 μM | 1.00 | 1.00 | 0.31 | 0.38 |
| (Q) | 1 μM | 0.97 | 1.00 | 0.53 | 0.69 |
| | 10 μM | 0.93 | 1.00 | 0.33 | 0.37 |
| (R) | 1 μM | 0.99 | 1.00 | 0.50 | 0.52 |
| | 10 μM | 0.95 | 0.93 | 0.11 | 0.11 |
| (S) | 1 μM | 0.91 | 0.99 | 1.00 | 0.94 |
| | 10 μM | 0.88 | 0.64 | 1.00 | 0.58 |
| (T) | 1 μM | 1.00 | 0.95 | 1.00 | 1.00 |
| | 10 μM | 1.00 | 0.70 | 1.00 | 0.53 |
| (U) | 1 μM | 0.84 | 0.78 | 0.94 | 0.93 |
| | 10 μM | 0.79 | 0.53 | 0.74 | 0.24 |
| (V) | 1 μM | 0.86 | 0.85 | 0.91 | 0.87 |
| | 10 μM | 0.77 | 0.53 | 0.75 | 0.20 |
| (W) | 1 μM | 1.00 | 0.85 | 0.98 | 0.86 |
| | 10 μM | 1.00 | 0.81 | 0.55 | 0.48 |

EXAMPLE 16

In Vitro Cytotoxicity of Potentiating Agents in Human KB Eoidermoid Carcinoma Cells The procedure for assaying the cytotoxicity of potentiating agents with human KB epidermoid carcinoma cells is essentially the same as the assay procedure described above for use with Chinese hamster ovary cells. In brief, KB 3–1 (wt) and KB V–1 (mdr) cells are plated at 500 cells/well in 96-well culture plates in Dulbecco's modified eagle medium, supplemented with 10% fetal calf serum. After 48 hours of incubation at 37° C., the media is changed and cells are treated with actinomycin D at 0.1 nM (3-1) or 20 nM (V-1). The test potentiating agent is introduced to one-half the untreated cultures and one-half the Act D treated cultures at 1 and 10 μM. After 96 hours of additional incubation at 37° C., 0.5 mg/ml MTT dye is added, the cells are incubated for three hours, after which the cells are dissolved in DMSO, and the absorbance is then read at 570 nm. The data is given in Table 2 below.

TABLE 2

In Vitro Cytotoxicity of Potentiating Agents in Human KB Epidermoid Carcinoma Cells

| Compound | Dose | Wildtype KB 3-1 | | Drug Resistant KB V-1 | |
|---|---|---|---|---|---|
| | | 0 | +ACT D | 0 | +ACT D |
| (A) | 1 μM | 0.99 | 0.88 | 1.00 | 0.99 |
| | 10 μM | 0.98 | 1.00 | 0.75 | 0.21 |
| (B) | 1 μM | 1.00 | 1.00 | 1.00 | 1.00 |
| | 10 μM | 0.83 | 0.91 | 0.44 | 0.01 |
| (C) | 1 μM | 1.00 | 0.78 | 1.00 | 0.97 |
| | 10 μM | 1.00 | 0.75 | 0.34 | 0.36 |
| (D) | 1 μM | 0.88 | 0.86 | 0.75 | 0.78 |
| | 10 μM | 0.51 | 0.65 | 0.36 | 0.01 |
| (E) | 1 μM | 0.89 | 0.85 | 0.88 | 0.74 |
| | 10 μM | 0.89 | 0.77 | 0.45 | 0.01 |
| (F) | 1 μM | 0.84 | 0.86 | 0.80 | 0.77 |
| | 10 μM | 0.78 | 0.68 | 0.59 | 0.12 |
| (G) | 1 μM | 0.87 | 0.80 | 0.86 | 0.91 |
| | 10 μM | 0.74 | 0.87 | 0.70 | 0.35 |
| (I) | 1 μM | 0.99 | 0.99 | 0.98 | 0.95 |
| | 10 μM | 0.30 | 0.40 | 0.34 | 0.04 |
| (J) | 1 μM | 0.89 | 0.85 | 0.88 | 0.74 |
| | 10 μM | 0.80 | 0.77 | 0.45 | 0.01 |
| (K) | 1 μM | 0.85 | 0.77 | 0.86 | 0.88 |
| | 10 μM | 1.00 | 0.03 | 0.08 | 0.13 |
| (L) | 1 μM | 1.00 | 1.00 | 0.98 | 1.00 |
| | 10 μM | 0.97 | 0.94 | 0.51 | 0.23 |
| (M) | 1 μM | 1.00 | 1.00 | 0.95 | 1.00 |
| | 10 μM | 0.96 | 1.00 | 0.65 | 0.31 |
| (O) | 1 μM | 0.79 | 0.81 | 0.74 | 0.78 |
| | 10 μM | 0.64 | 0.73 | 0.07 | 0.06 |
| (P) | 1 μM | 0.65 | 0.72 | 0.73 | 0.72 |
| | 10 μM | 0.65 | 0.71 | 0.52 | 0.58 |
| (Q) | 1 μM | 0.92 | 0.91 | 0.86 | 0.83 |
| | 10 μM | 0.77 | 0.78 | 0.80 | 0.65 |
| (R) | 1 μM | 0.78 | 0.84 | 0.87 | 0.90 |
| | 10 μM | 0.36 | 0.34 | 0.06 | 0.02 |
| (S) | 1 μM | 0.77 | 0.79 | 0.89 | 0.84 |
| | 10 μM | 0.67 | 0.72 | 0.72 | 0.48 |
| (T) | 1 μM | 0.86 | 0.90 | 0.96 | 0.92 |
| | 10 μM | 0.81 | 0.83 | 0.84 | 0.64 |

EXAMPLE 17

Formulations

In the formulations of this Example the active compound is a compound of Formula (I) described hereinbefore.

| (A) - Injectable | |
|---|---|
| Ingredient | Amount Per Ampoule |
| Active Compound | 1.0 mg |
| Water for Injections | 1.0 mL |

The finely ground active compound is dissolved in the water for injections. The solution is filtered and sterilized by autoclaving.

| (B) - Syrup | |
|---|---|
| Ingredient | Amount Per Ampoule |
| Active Compound | 1.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Colouring | q.s. |
| Water | Q.S. to 5.0 mL |

Ethanol, sucrose, sodium benzoate, methylparaben, and flavouring are combined in 70% of the total batch quantity of water. Colouring and the active compound are dissolved in the remaining water, then the two solutions are mixed and clarified by filtration.

| (C) - Tablet | |
|---|---|
| Ingredient | Amount Per Tablet |
| Active Compound | 1.0 mg |
| Lactose | 110.0 mg |
| Corn Starch, Pregelatinized | 2.5 mg |
| Potato Starch | 12.0 mg |
| Magnesium stearate | 0.5 mg |

The active compound is finely ground and intimately mixed with the powdered excipients lactose, corn starch, potato starch and magnesium stearate. The formulation is then compressed to afford a tablet weighing 126 mg.

| (D) - Capsule | |
|---|---|
| Ingredient | Amount Per Capsule |
| Active Compound | 1.0 mg |
| Lactose | 440.0 mg |
| Magnesium Stearate | 5.0 mg |

The finely ground active compound is mixed with the powdered excipients lactose and magnesium stearate and packed into gelatin capsules.

| (E) - Nasal Spray | |
|---|---|
| Ingredient | Amount Per 100.0 mL |
| Active Compound | 1 g |
| Sodium Chloride | 0.8 g |
| Preservative | 0.5 g |
| Purified Water | 100.0 mL |

The preservative is dissolved in warm purified water and after cooling to 25°-30° C. the sodium chloride and active compound are added. The pH is then adjusted to 5.5-6.5 and purified water is added to bring the final volume to 100.0 mL.

The foregoing Examples are illustrative of the present invention, and are not to be taken as restrictive thereof. The invention is defined by the following claims, with equivalents of the claims to be included therein.

That which is claimed is:

1. A method of combating multiple drug resistance of susceptible tumor cells resistant to vinca alkaloids in a subject in need of such treatment, comprising administering to the subject a compound, in an amount effective to combat multiple drug resistance of tumor cells sensitive to said compound, wherein said compound is of the formula:

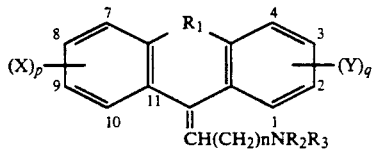

wherein:

$R_1$ is selected from the class consisting of —CH$_2$CH$_2$—, —CH$_2$O—, —OCH$_2$—, —NHCH$_2$—, and —CH$_2$NH—;

X is selected from the class consisting of hydrogen and halogen;

Y is selected from the class consisting of hydrogen and halogen;

n is from 0 to 3;

each of p and q is from 1 to 4; and $R_2$ and $R_3$ are each independently selected from the class consisting of hydrogen and $C_{1-4}$ alkyl, or together with the nitrogen atom form a nitrogen-containing heterocyclic ring having four to six ring members;

or a pharmaceutically acceptable salt thereof.

2. A method according to claim 1, wherein $R_1$ is selected from the group consisting of —CH$_2$— and —OCH$_2$—.

3. A method according to claim 1, wherein said compound is (Z)-1-[2-Bromo-6,11-dihydrodibenz[b,e]oxepin-11-ylidene)ethyl]pyrrolidine.

4. A method according to claim 1, wherein said tumor cells are adenocarcinoma cells.

* * * * *

UNITED STATES PATENT AND TRADEMARK OFFICE
CERTIFICATE OF CORRECTION

PATENT NO. : 5,300,282                              Page 1 of 2
DATED     : April 5, 1994
INVENTOR(S) : Ann C. King It is certified that error appears in the above-identified patent and that said Letters Patent is hereby corrected as shown below:

Column 1, Line 36, after Approach add --to the--.

Column 2, Line 22, correct " inventor,s " to read -- inventor's --.

Column 3, Line 54, correct " R " to read -- $R_1$ --.

Column 4, Line 44, correct " [b.e] " to read -- [b,e] --.

Column 4, Line 50, correct " [b,3] " to read -- [b,e] --.

Column 10, line 30, "H );" (4th occurrence) should read --$H_4$ )--.

Column 10, Line 49, correct " H of 10% " to read -- $H_4$ of 10% --.

Column 11, Line 47, correct "stream" to read -- steam --.

Column 12, Line 26, correct "(E)//Z)" to read -- (E)/(Z) --.

Column 14, Line 64, after (1.6M), take out "lo".

Column 15, Line 41, correct "o-5" to read -- $\alpha$-5 --.

Column 15, Line 63, correct "6:6.76" to read -- $\delta$:6.76 --.

Column 16, Line 39, correct "3 29" to read -- 3:29 --.

Column 16, Line 60, correct "H of 2%" to read -- $H_4$ of 2% --.

UNITED STATES PATENT AND TRADEMARK OFFICE
CERTIFICATE OF CORRECTION

PATENT NO. : 5,300,282

DATED : April 5, 1994

INVENTOR(S) : Ann C. King

It is certified that error appears in the above-identified patent and that said Letters Patent is hereby corrected as shown below:

Column 17, Line 47, correct "AuxBI" to read -- AuxB1 --.

Column 18, Line 60, correct "Eoidermoid" to read -- Epidermoid --.

Signed and Sealed this

Sixth Day of September, 1994

*Attest:*

BRUCE LEHMAN

*Attesting Officer*     *Commissioner of Patents and Trademarks*